US00PP08016P

United States Patent [19]

Falstad, III

[11] Patent Number: Plant 8,016

[45] Date of Patent: Oct. 27, 1992

[54] *HOSTA PLANTAGINEA* — "GOLD MARGIN" VARIETY

[76] Inventor: Clarence H. Falstad, III, 152 Birchwood, Holland, Mich. 49423

[21] Appl. No.: 572,681

[22] Filed: Aug. 24, 1990

[51] Int. Cl.[5] ..... A01H 5/00
[52] U.S. Cl. ..... Plt./68.1
[58] Field of Search ..... Plt./68

[56] References Cited

U.S. PATENT DOCUMENTS

P.P. 2,467 1/1965 Grullemans ..... Plt. 68

OTHER PUBLICATIONS

Anon. "Wayside Gardens" (catalog) Fall 1979 The Wayside Gardens Co., Hodges, S.C. p. 68.
Aden, P. "1978 List" (catalog) Aden's Plants, Paul Aden, Baldwin, N.Y. pp. 1-6.

*Primary Examiner*—James R. Feyrer
*Attorney, Agent, or Firm*—Waters & Morse

[57] ABSTRACT

A new variety of *Hosta plastaginea* characterized by a gold to lime green margin on a darker green leaf and a thicker, more rigid, and more coriaceous leaf structure, giving the plant a more upright habit than the original species.

1 Drawing Sheet

SUMMARY BACKGROUND, AND ORIGIN OF THE INVENTION

The new variety is a tissue culture derived sport of the species *Hosta plantaginea*. I discovered the plant in a cultured state in a greenhouse on the premises of Walters Gardens, Inc., Zeeland, Mich., among a group of transplanted propagules produced from a plant tissue culture laboratory. The stock plant was from *Hosta plantaginea* which had begun producing mutant sports of a mixture of variegations including those of a sectorial, mericlinal and periclinal nature. A single plant with a stable periclinal variegation was noticed in the summer of 1988 and was separated from the rest of the transplants. Continued observations led to a greater recognition of the uniqueness of the plant.

The cultivar has been asexually propagated via tissue culture at a nursery in Zeeland, Mich. It has also been asexually propagated by division of the rhizome. Although tissue culture propagation can produce aberrants or mutants, making some culling necessary, to one skilled in the art of tissue culture it can also be a propagation tool useful in producing identical plants.

By using the method developed and improved at a nursery in Zeeland, Mich., the Hosta 'Gold Margin' variety is being successfully propagated so as to produce plants that are substantially identical to the original plant by tissue culture division as well as by garden division of the rhizome.

The new variety is hereby named "Gold Margin" and is sold under the trademark "Heaven Scent".

BRIEF DESCRIPTION OF THE DRAWINGS

The invention is illustrated in the attached photographic drawings in which.

Botanical Description of the Plant

Figure 2:
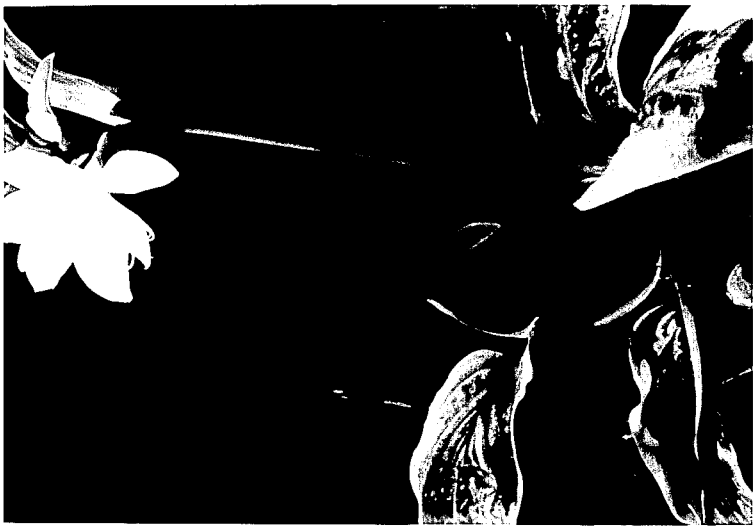
FIG. 1 shows the plant from a perspective above the plant and FIG. 2 shows the plant from a side elevational perspective.
Figure 1:
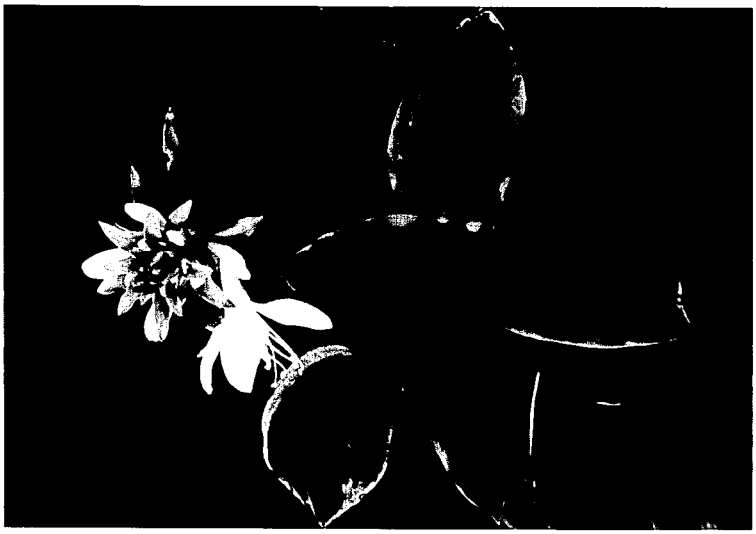

*Hotas plantaginea* is a densely rhizomatous herbaceous perennial with a short subterranean stem and petioled, tufted leaves. The glossy surfaced leaves are ovate to cordate-ovate and have nine (9) to eleven (11) vein pairs and are a uniform dark green in color, essentially the same color as the dark green central portions of the leaves of the present invention. Leaf dimensions are approximately nine and one-half (9½) inches to ten (10) inches long and six and one half (6½) inches to seven (7) inches wide. Foliage height is approximately twenty (20) inches to twenty-four (24) inches and bears twenty-six (26) to thirty (30) white fragrant funnelform flowers, each three (3) to five (5) inches long, on a thirty (30) inch capitate raceme or rarely panicle. The dimensional and flower number are dependent on environmental conditions and cultural practices, and therefore may be slightly greater or smaller. The flowers bloom in Michigan from mid-August to mid-September. Flower characteristics and fragrance are identical to those of the parent species.

The species *Hosta plantaginea* is quite uniform in appearance and does not have a large number of varieties or subspecies. The principal form of the plant is generally known by the species name *Hosta plantaginea*. Some variants that have been developed have been given distinct variety names. There appear to be two forms of the principal species that is called *Hosta plataginea*. These appear the same and are differentiated only by the size of the flower. One size is considered to be the normal or average form and the other is considered to be larger than normal. The present invention was derived from the normal form of the species known as *Hosta plantaginea*.

*Hosta plantaginea* is one of only two species of this genus that are native to, and only to, the mainland of China. The other species, *Hosta ventricosa*, flowers much before *Hosta plantaginea*, thus preventing any likelihood of interspecific cross pollination. All other species discovered to date have come from either the islands of Japan or a few from those of Korea. Being so geographically isolated, an intrabreeding species population will tend to become more identical.

*Hosta plantaginea* also has many traits consistent with a plant of a tetraploid nature (having twice the normal compliment of chromosomes). A natural doubling of the chromosomes would tend to produce a more homozygous population resulting in nearly identical appearing individuals.

The new variety shares the foregoing characteristics with its parent, but is a unique and improved form of the original plant species, *Hosta plantaginea,* in two principal aspects. First, the new variety is a distinct and stable chimera with a lighter yellowish margin and a green central portion of the leaves. The second distinction is that of an improved substance or increased thickness of the leaves.

The variegation in the plant varies in color from spring through autumn. As the leaves emerge in the spring, the color difference between the margin and the center of the leaf is barely discernable. The margin color proceeds to lighten as the growing season progresses, and by mid-summer with the plant grown in the proper shade, the margin color is more grey than Sap Green 62 as defined by The Royal Horticultural Colour Chart and more yellow than Pod Green 061. The leaf center is slightly darker than Scheeles Green 860 or about 960. An intermediate color, a Scheeles Green 860/2, is frequently exhibited at a position between the margin and center of the leaf. This is the result of a type of lamination of cell layers with differing amounts of pigment coming from two distinct histogenic regions of the meristem.

The margin tissue generates from the outer layer of the meristem usually referred to as the L-1 layer. The inside portion of the leaves is comprised of the second layer in the meristematic dome, usually called the L-2 layer. When the leaf primordia is developing, some regions either of the L-1 or L-2 may grow faster than the corresponding region, producing a section of the leaf with either a wider margin or enlarged center. Likewise, when the meristem layers occupy the same location (between the margin and the center) the L-1 layer determines the surface of the leaf, either the adaxial, abaxial, or both, and the L-2 produces the medial portion of the leaf. This inconsistent development of the meristematic, or histogenic, regions tends to produce the typical lacerated effect of the margin, the varying widths, and also the normal but irregular evidence of the intermediate colors.

When grown in more sun or higher light intensity, the margin in mid-summer is a Sulfur Yellow $\frac{1}{3}$, and the center is Lettuce Green 661.

The margin variegation, although stable, is uniformly irregular and frequently protrudes toward the midrib. The width of the margin varies in measure from very thin on an immature plant to an irregular three-eighths ($\frac{3}{8}$) inches to three-quarters ($\frac{3}{4}$) inches or more on a mature specimen. A young plant may have thin margins on the first leaves and develop wider margins on the older leaves of those produced later in the season. The leaves produced later in the season tend to be more typical of the mature version.

Environmental conditions, cultural practices, and growth rate also affect the extent, color, and width of the margin.

Typical of plants in the genus Hosta, the petiole is more like an extension or modification of the leaf. As such, it has the same variegation with a few minor variations. The petiole is more protected from the sun and thus the lighter color darkens, or does not bleach as much. Also, because there is much less width for the variegation to spread out, the intermediate color is not present, and the jaggedness is not visible.

A second distinctive characteristic of the new variety is an improved substance or thickness of the leaves. While the original species has a soft, flexible, thin leaf that tends to droop or bend downward, the present cultivar is more rigid and stiff. The leaf of the present variety is thicker and more coriaceous than the original species. This gives the leaves a more upright habit than the original species, with the leaves tending to extend more upwardly instead of bending or drooping downwardly. The substance and leaf thickness of the parent species are the same as shown in applicant's co-pending application for the White Margin variety (Ser. No. 540,816, filed Jun. 16, 1990), which is incorporated by reference.

The growth of Hosta 'Gold Margin' is essentially the same as that of the parent species, *Hosta plantaginea.* Mature height and size of the leaves is slightly reduced; however, vigor is not noticeably changed. Like the parent species, the plant grows better with ample water, but an established specimen can withstand some brief periods of drought. Flowering is more prolific with more sun, but in Zeeland, Mich. growth is best with light shade during the hottest part of the day. The plant is resistant to most diseases and can survive sub-zero temperature. The foliage is not frost hardy and can be affected by late spring frosts. All other aspects of the plant including flowering and seed production are identical to the parent species.

I claim:

1. The new and unique variety of the plant *Hosta plantaginea,* substantially as described and illustrated.

* * * * *